United States Patent [19]

Haas

[11] 4,153,418
[45] May 8, 1979

[54] CHEMICAL TRACER METHOD OF AND STRUCTURE FOR DETERMINATION OF INSTANTANEOUS AND TOTAL MASS AND VOLUME FLUID FLOW

[76] Inventor: Rudy M. Haas, 8171 Forestlawn, Detroit, Mich. 48234

[21] Appl. No.: 737,080

[22] Filed: Nov. 1, 1976

Related U.S. Application Data

[60] Division of Ser. No. 349,622, Apr. 9, 1973, Pat. No. 3,988,926, which is a continuation-in-part of Ser. No. 141,749, May 10, 1971, Pat. No. 3,727,048.

[51] Int. Cl.² .................. G01F 1/70; G01N 31/00
[52] U.S. Cl. .................. 23/232 R; 73/194 M
[58] Field of Search ............ 23/232 R, 232 E, 254 R, 23/254 E; 73/194 M, 194 E

[56] References Cited

U.S. PATENT DOCUMENTS

| | | | |
|---|---|---|---|
| 3,545,270 | 12/1970 | Chang | 73/194 B |
| 3,881,351 | 5/1975 | Prachar | 73/194 |

Primary Examiner—Herbert Goldstein
Attorney, Agent, or Firm—Whittemore, Hulbert & Belknap

[57] ABSTRACT

The method of determination of the total mass flow of at least one component of interest in a reacted flowing main fluid in a period of time comprising the introduction of an analyzable tracer component at a known mass rate into a flowing main fluid, mixing the tracer component with the flowing main fluid, reacting the mixture of the tracer component and flowing main fluid in a reactor, analyzing the reacted mixture to determine the concentration of at least the tracer compónent and one component of interest in the reacted mixture, and time integrating the product of the ratio between the component of interest concentration and the tracer concentration, and the mass flow rate of the tracer over the time period. The fluid flow rate of the reacted flowing main fluid may be slowly changing and the component of interest may be a reacted fuel which may be a fossil fuel or a reaction product thereof or of the flowing main fluid.

7 Claims, 4 Drawing Figures

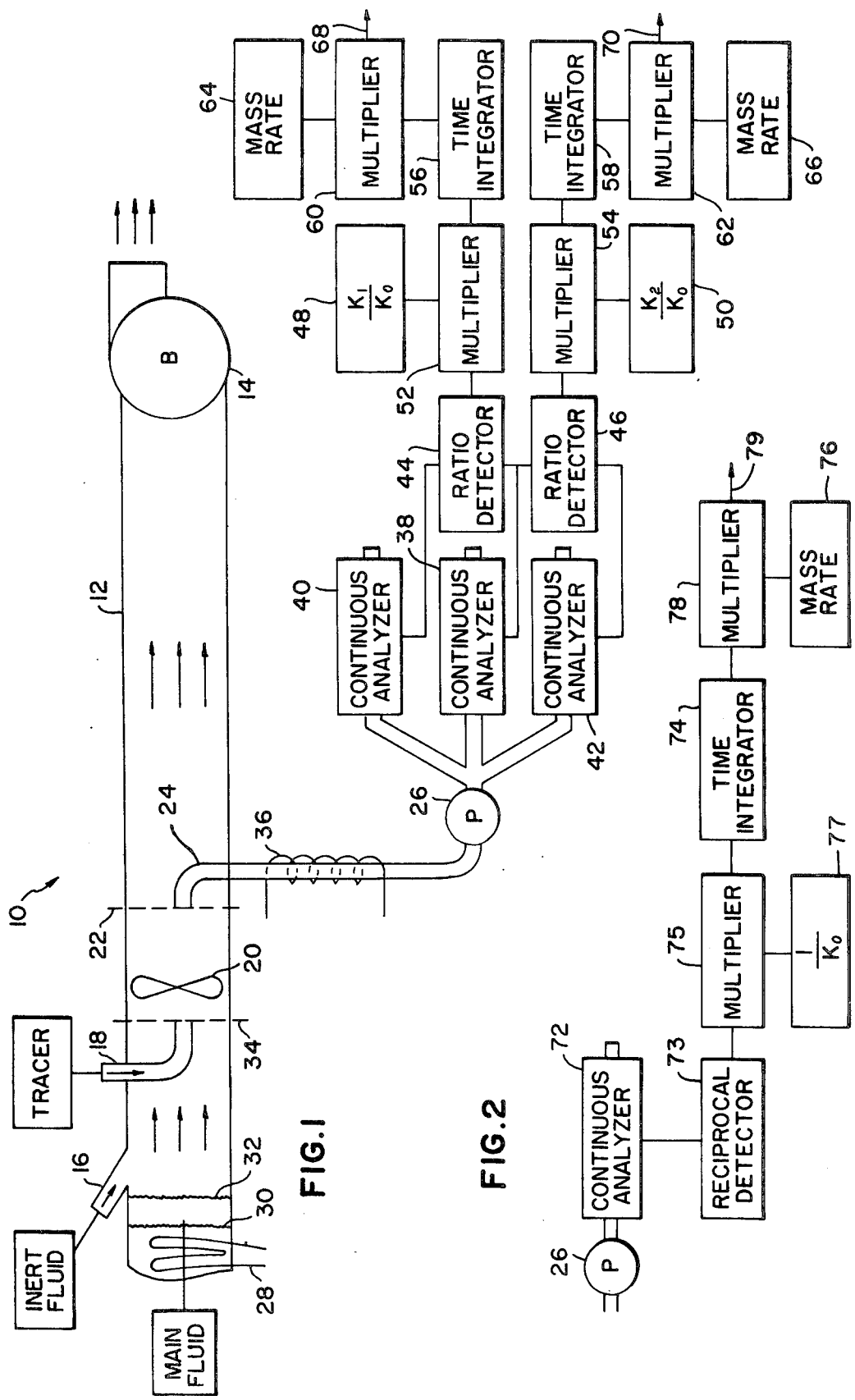

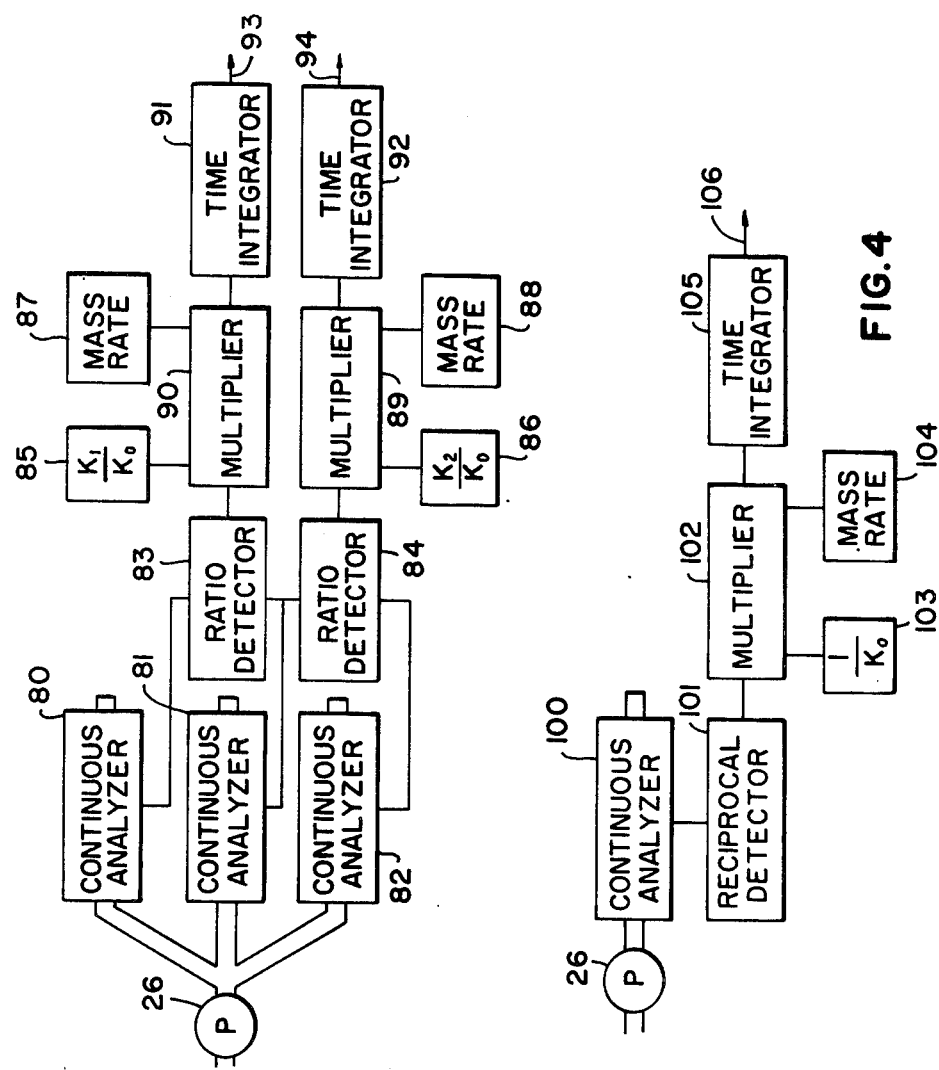

CHEMICAL TRACER METHOD OF AND STRUCTURE FOR DETERMINATION OF INSTANTANEOUS AND TOTAL MASS AND VOLUME FLUID FLOW

CROSS REFERENCE TO RELATED APPLICATIONS

This application is a division of application Ser. No. 349,622, filed Apr. 9, 1973, now U.S. Pat. No. 3,988,926, which is a continuation-in-part of application Ser. No. 141,749, filed May 10, 1971, now U.S. Pat. No. 3,727,048.

BACKGROUND OF THE INVENTION

1. Field of the Invention

The invention relates mainly to determination of mass flow of selected components of a fluid and refers more specifically to a chemical tracer method of determination of total mass flow of selected fluid components in automobile exhaust pipes, smokestacks, pipe lines and the like. One of the advantages of the method of the invention is that the flow rate, pressure and temperature of the fluid can vary in many cases during practice of the method with the structure disclosed.

2. Description of the Prior Art

In the past, most approaches to air pollution control through the measurement of total emission and regulation thereof by government agencies and the like have required a knowledge of both concentration and total volume of emission. It is preferable, however, to have knowledge of the total mass emission of each component of interest without the necessity of determining the total volume of emission. This is especially true in determining mass emission from industrial smokestacks, automobile tailpipes and industrial and community sanitary systems.

SUMMARY OF THE INVENTION

In accordance with the invention, total mass flow of selected components in a main fluid flow are determined by insertion of a chemical tracer into the main fluid flow, analyzing the main fluid flow after the insertion of the tracer therein, providing ratios of the tracer component to each of the components of interest in the total fluid flow, multiplying by the mass flow rate of the chemical tracer inserted in the main fluid flow, and integrating the ratios with respect to time. Total particulate mass flow and total volume flow as well as instantaneous mass, particulate mass and volume flow may be determined by similar methods and structures for effecting the methods similar to the structure illustrated.

In determining total mass flow of one or more of the many components present, calculations become simpler if one or more of the following variables are held constant, i.e., pressure, temperature, main fluid flow rate, tracer injection rate and tracer flow rate. When the total volume flow of a component of interest is known between determined times, the total volume flow between other times may also be determined in accordance with the invention. When the tracer injection rate varies, difficulties are encountered which do not exist when the injection rate is constant.

BRIEF DESCRIPTION OF THE DRAWINGS

FIG. 1 is a partially diagrammatic and partially block diagram of structure constructed in accordance with the invention for determination of total mass, particulate mass and volume flow of selected components of a fluid by chemical tracer methods in accordance with the invention.

FIG. 2 illustrates a modification of the structure of FIG. 1 particularly suited to determining total volume flow by the method of the invention.

FIG. 3 illustrates a modification of the structure of FIG. 1 particularly suited to determining the instantaneous and total mass, particulate mass and volume flow of selected components of a fluid when the mass injection rate of tracer is variable in accordance with the invention.

FIG. 4 illustrates a modification of the structure of FIG. 1 particularly suited to determining total volume flow when the mass injection rate of the tracer is variable in accordance with the invention.

DESCRIPTION OF THE PREFERRED EMBODIMENTS

The structure 10 for determining the total mass flow, over a selected time, of a component of interest in a main fluid flow illustrated in FIG. 1 includes a main fluid flow tube 12 through which the fluid to be analyzed is passed. The fluid to be analyzed may be drawn through the tube 12 by means of the blower 14 or similar apparatus to provide a uniform flow rate for the main fluid. If the flow in the main flow tube 12 is not sufficiently constant (in the case of a gas, this would mean variations in pressure) to fill this tube, additional inert fluid may be injected into the main fluid flow through the tube 16 connected to the tube 12 as shown. Thus, the main fluid flow rate may more easily be maintained constant.

A tracer which disperses readily in the main fluid flow and is readily analyzable is injected into the main fluid flow tube 12 through the tracer injection tube 18 substantially centrally of the main tube 12. The exact location of the tracer injection tube does not have to be as shown in FIG. 1. The tracer can be injected through tube 16, or it can be injected prior to the site of the inert fluid inlet tube 16 with the restriction that no fluid enters at the inert fluid inlet 18, or the tracer inlet 18.

The main fluid flow, inert fluid if any, and injected tracer are mixed by mixer 20. Theorectically the tracer is thus uniformly distributed over the cross section 22 of the main flow tube 12. A sample of the mixed tracer and main fluid (assuming no inert fluid is necessary) is withdrawn from the main fluid flow tube 12 through the sample tube 24 and is passed to the pump 26. In place of removing a sample for analysis, an analyzing signal, e.g., radiation, can be transmitted from or into the main flow tube at the hypotheoretical cross sectional area 22.

Prior to the tube 16, a heat exchanger 28, a particle filter 30 and a condenser 32 can be provided to prevent volume changes, particle deposition, or condensation, respectively, before or in the analyzers. The main fluid flow may be maintained at a constant temperature by the heater 28, and other heaters lining the main fluid flow tube, if needed, undesirable particles are filtered therefrom and moisture is condensed therefrom prior to injection of the tracer thereinto at the cross section 34 of the tube 12.

If the tracer is a fossil fuel which is also to be used for heat production as in a furnace (to be considered as a reactor for our purposes), it will be injected into the reactor located prior to the main flow tube.

If coal is the fuel, its mass injection rate can be measured as it comes into the furnace, e.g., it can be brought to the furnace at a known mass rate on a conveyor belt.

In addition, a heater 28, 36 or other may be provided anywhere in the apparatus 10 to maintain the temperature of the main fluid flow aand/or sample substantially constant.

The sample of the tracer and main fluid is passed through the pump 26 to the continuous analyzers 38, 40 and 42. Analyzers 38, 40 and 42 for analyzing the concentration of tracer and the concentration of two components of interest in the main fluid flow respectively are well-known items of commerce and will not be considered in detail herein, except to say that the analyzers should be linear or should be linearized. The analyzers can be of a flow or non-flow rate dependent variety. Analyzers of the non-dispersive infrared or ultraviolet type are well suited to this type of analysis and may be purchased from The Beckman Instrument Company as Model 315, nondispersive infrared analyzer. The continuous analyzers will provide an output signal which is proportional to and varies in accordance with the concentration of the tracer and components of interest in the main fluid flow tube 12 at cross section 22. If the output signal of the analyzer used is not linear with respect to the concentration, a linearizing electronic circuit, a calibration curve equation along with a computer, or in the case of a photometric analyzer, a signal proportional to a log of the reciprocal transmission may be used.

The signals from the analyzers 38 and 40 and from the analyzers 38 and 42 are passed to ratio determining circuits 44 and 46 from which signals proportional to and varying in accordance with the ratio of the concentration of tracer to the concentration of the separate components of interest of the main fluid flow at the cross section 22 are provided. The ratio signals are then multiplied by desired proportionality factors between circuit parameter values, $K_0$, $K_1$ and $K_2$ which are constants if the analyzer output signal is linear or become constants when the analyzer signal is linearized from circuits 48 and 50 in multipliers 52 and 54. The signals from the multipliers 52 and 54 are then integrated over the time the total masses of the components of interest are desired in the integrators 56 and 58. The integrated signals are subsequently multiplied in multipliers 60 and 62 by signals proportional to the constant mass rate of injection of tracer into the main fluid from circuits 64 and 66 to provide output signals on conductors 68 and 70 representative of the total mass of the components of interest during the time of integration.

In the apparatus of FIG. 1, the tracer can be injected at a known constant mass rate in order to measure the total mass flow over the time period of interest. If the fluid flow rate is constant, the concentration of the tracer can be brought outside the integral sign where the ratio of the mass injection rate of the tracer to its resulting concentration is a constant. This apparatus can also be used to obtain the total volume flow of a fluid by setting the concentration of the component of interest, $C_1$, equal to 1. In addition, the apparatus can also be used to obtain instantaneous mass and volume flow rates by not integrating over a period of time. If the mass injection rate is constant for the tracer, the flow rate of the fluid in the main flow tube does not have to be constant, but it is preferred that it be constant. If the injection rate of the tracer varies with time, the fluid flow rate should be as constant as possible for greatest accuracy, using the prescribed mathematical equation for the calculation. A time delay device or its equivalence must be present in order to relate, for the purpose of calculating the concentrations of both the tracer and the components of interest to the known mass injection rate of the tracer responsible for its concentration at the designated cross sectional area. In other words, for greatest accuracy, the tracer mass injection rate must equal the mass flow rate of the tracer passing the cross sectional area most of the time, not necessarily at the same instant of time, but this difference in time must be determinable if it is significant in the calculations. The tracer injection rate may be based on the required concentration needed to give satisfactory analytical results for the analyzer to be used. In the apparatus of FIG. 3, the tracer may be injected at a known variable mass rate.

With a variable mass injection rate of tracer, a sample of the tracer, main fluid, and inert fluid if needed, is passed through the pump 26 to the continuous analyzers 80, 81 and 82. Analyzers 80, 81 and 82 are equivalent to the analyzers 40, 38 and 42 in FIG. 1.

The signals from the analyzers 80 and 81 and from the analyzers 81 and 82 are passed to ratio determining circuits 83 and 84, which are equivalent to the ratio determining circuits 44 and 46 in FIG. 1, from which signals proportional to and varying in accordance with the ratio of the concentration of tracer to the concentration of the separate components of interest of the main fluid flow at the cross section 22 are provided. Each of the output signals from ratio detectors 83 and 84 are then multiplied in multipliers 89 and 90 by the desired proportionality factors between circuit parameter constants, $K_0$, $K_1$ and $K_2$ from circuits 85 and 86, and by signals proportional to the mass rate of injection of tracer into the main fluid from circuits 87 and 88. The signals from the multipliers 89 and 90 are then integrated in the integrators 91 and 92 to provide output signals on conductors 93 and 94 representative of the total mass flow of the components of interest during the time of integration.

The tracer, which may be continuously analyzed as carbon dioxide and injected at a know constant mass rate of a fossil fuel, equivalent to a known constant mass rate of carbon dioxide, when the main fluid is air and the tracer oxidation products are combustion gases, should pass the cross sectional area 22 at the same rate as the tracer is injected into the main fluid flow tube 12 at the cross section 34.

The fluid flow to the continuous analyzers 38, 40 and 52 must originate from the same volume in the main fluid flow tube 12, and should arrive at each analyzer for analysis at the same time. As before, the flow time for the sample to pass from the main flow tube to the point of analysis in the analyzer must also be considered when substituting data in the proper equations, otherwise, part or all of the data at the analyzers must be stored and subsequent calculations must be conducted with the stored data sometime in the future.

The tracer injection may be a pure component or a mixture having a pure tracer component plus an inert ingredient. The "pure" tracer component itself can be a mixture having a known composition, with or without inert ingredients, e.g., a fossil fuel. In addition, the tracer must be accurately qualitatively and quantitatively analyzable on a continuous basis and should not undergo a chemical change unless the extent of the chemical reaction is known and its products are easily analyzable. An example of this latter would be the use of a fossil fuel which undergoes a combustion reaction and the products such as carbon dioxide, are analyzed.

When a constant injection rate is referred to for the tracer, an effectively constant mass injection can be thought of, i.e., periodic injection with mixing, to give an equivalent to an actual constant mass injection, should be considered to be the same for our purposes. The tracer component which is to be used, will of course depend on the overall system in which it is to be injected. It can be (1) a stable or unstable element, or compound, (2) one that fluoresces, phosphoresces, or emits radiation or particles, or (3) one that absorbs mass or electromagnetic radiation or the like, or particles such as neutrons, protons, positrons, or the like. The physical state of matter of the tracer would not have to be the same as that already present in the main fluid flow tube, e.g., a liquid soluble gas or solid can be injected into a liquid.

The linear flow velocity in the sampling line 24 does not have to be equal to that of the linear flow velocity in the main fluid flow tube 12, but it should be constant and preferably greater than that in the main fluid flow tube, but not excessively greater, otherwise fluid far removed of what is at the cross sectional area 22 will be removed.

If the flow is much slower than that in the main flow tube, large, sudden concentration changes may not register accurately enough, thereby giving results very different than what is actually in the main flow tube. Isokinetic sampling usually would be preferred.

The sample analysis can be done directly on the main flowing fluid, e.g., by passing a beam of electromagnetic radiation through it where both the tracer and component of interest are absorbed at certain wavelengths. In addition, conditions which are established in the standardization of the analyzers 38, 40 and 42 such as temperature and pressure must not vary before the unknown mixtures have been analyzed.

The pump 26 for the continuous analyzers should be of a non-contaminating and non-corrosive material. A diaphragm-type pump is generally satisfactory. Other types of pumps may be required to maintain consistency in flow in both the main fluid flow tube 12 and in the sample flow tube.

In addition to analyzers of the spectrophotometric type, etc., those of an electrode type such as a calcium or water hardness specific ion electrode mainly for liquids are also being considered. In addition, electrodes for gas monitoring are also suitable, if available, since they can also be used to determine concentration (i.e., activity) directly when in conjunction with an E.M.F. measuring circuit.

Where it is stated that a tracer is injected at a known mass rate, in addition to what is usually meant, it is also understood to mean that the tracer can enter the flowing fluid stream: (1) due to formation of a substance as a result of physical or chemical reation, resulting from the introduction of energy, such as electricity, heat, radiation, etc., or (2) by decomposing a substance not part of the flowing fluid but in contact with it, such as dissolution of an electrode with electrical energy, always at a known rate.

The injected tracer can also be a mixture of two or more tracers, where each of the tracers is used for determining the mass of one or more components of interest. One of the advantages would be where two or more multicomponent analyzers, e.g., mass spectrometer and chromatographs are used where each can analyze the tracer and one component of interest with ease while the other component may be difficult to analyze with the same analyzer.

Thus, in operation of the apparatus 10, a fluid such as automobile engine exhaust gas is passed into the main fluid flow tube 12 past the temperature control structure 28 where the temperature is made constant. Particles are filtered from the exhaust and any moisture therein is condensed by the filter 30 and condensation structure 32, or it may be made constant by adding a stream of water vapor and the like.

If the quantity of exhaust gas is not sufficient to provide a constant flow rate in the main fluid flow tube 12, an additional inert gas can be injected into the fluid flow tube 12 through the tube 16 sufficient to provide a constant total fluid flow through the main fluid flow tube 12, if this is needed or preferred.

On passing the cross section 34 in the main fluid flow tube 12, a tracer chemical such as carbon dioxide is injected into the main fluid flow at a known mass rate. A known mass rate may be maintained by the use of known flow rate devices such as a critical orifice, a constant diffusion permeation tube, or a constant energy addition producing a constant mass rate of another substance, e.g., an electrochemical decomposition, etc., which will not be considered in detail herein.

The main fluid flow and tracer are mixed by mixer 20 to provide a uniform mixture at the cross section 22 of the main fluid flow tube 12. After passing the sample tube 24 at the cross section 22, the main fluid flow is usually passed through the blower or pump 14 and is exhausted from the main fluid flow tube 12. A blower is usually satisfactory for gases and a transfer pump for liquids. In some cases, no pumping system 14 is necessary because of some other driving force.

The sample of the mixed main fluid flow and tracer is passed through pump 26 to the continuous analyzers 38, 40 and 42 which analyze the concentration of the tracer and the components of interest in the main fluid flow. The electrical signals from the analyzers are passed to the ratio determining circuits 44 and 46, so that out of the ratio determining circuits 44 and 46 a signal equal to a ratio of the concentration of the components of interest to the tracer concentration in the main fluid flow is provided.

These ratio signals are then multiplied by signals from the circuits 48 and 50 to compensate for the electrical differences in the analyzer circuits and are subsequently integrated by integrators 56 and 58 over the time that the total mass flow of the components of interest of the main fluid flow is desired. The integrated signals from the integrators 56 and 58 are subsequently multiplied in the multipliers 60 and 62 by a signal representing the mass flow rate of the tracers 68 and 66 to provide the conductors 68 and 70 with a signal representing the total mass of the components of interest flowing in the main fluid flow over the time of integration. This electronic signal can be fed to a digital readout, a paper printer, a computer, etc., or can be used to actuate an electronic switch.

Under the circumstance where the mass injection rate of the tracer is not constant over the time period of integration, the tracer injection rate must be multiplied by the ratio of the analyzer signals before integration, or both the tracer concentration and tracer injection rate can be outside the integral sign for a constant fluid flow rate.

The operation of the apparatus 10 can be mathematically shown to be theoretically correct. Thus, the relationship of mass ($m_1$), volume ($V_1$), and concentration ($C_1$), of a component of interest, with concentration expressed as mass per unit volume, is given below:

$$m_1 = C_1 V_1$$

The same relationship holds for the tracer component and is shown by the equation:

$$m_o = C_o V_o$$

Since the volume of tracer component and the component of interest in the sample are the same, V is the same as indicated by the equation:

$$V_1 = V_o = V$$

Therefore, $m_1 = C_1/C_o m_o$ wherein $C_1$ and $C_o$ are both considered to be at the same temperature and pressure since both are referred to the same uniform composition which therefore is considered to be the same chemically and physically throughout.

The instantaneous mass flow rate of the component of interest, that is, $(dm_1/dt)$ passing through the cross sectional area 22 can be expressed as a function of $C_1$, $C_o$ and $(dm_o/dt)$ where $(dm_o/dt)$ is the instantaneous flow rate of the tracer, in units of mass per unit time:

$$(dm_1/dt) = C_1/C_o (dm_o/dt)$$

In this equation, $C_1/C_o$ is the proportionality factor relating mass of the tracer component transferred across the cross sectional area 22 to the mass of the component of interest also transferred across the same area where some, all, or none of the above four values may be time dependent.

The total mass flow of component one, that is, $m_1$ from $t_1$ to $t_2$, is obtained by the integration of the above equation to give $$\int_{(m_1)_{t_1}}^{(m_1)_{t_2}} dm_1 = \int_{t_1}^{t_2} \left(\frac{dm_o}{dt}\right) \frac{C_1}{C_o} dt$$

If the mass injection rate of the tracer is not constant, then the total fluid flow rate should be constant, nearly constant, or changing slowly. It is then possible to relate the mass injection rate of the tracer in the above equation to the concentration of the tracer it produces. If there is a large change in the flow rate of the fluid in a short period of time, collection and use of data with a high degree of accuracy becomes difficult. This is the case with both a constant and a variable mass injection rate of tracer.

From this equation it is evident that in a system with a constant flow rate, the ratio of $$\left(\frac{dm_o}{dt}\right)/C_o$$

is a constant in both cases, (1) where the mass injection rate of the tracer is constant, and (2) where the injection rate is not constant but where the analyzed concentration is related back to what the injection $(dm_o/dt)_o$ was that produced it.

Since the mass flow rate of the tracer through the cross sectional area 22, $(dm_o/dt)$, can be adjusted to be and remains the same as the constant mass injection rate of the tracer $(dm_o/dt)_o$, that is to say, $(dm_o/dt)_o$ = a constant. Therefore, $$(m_1)_{t_2} - (m_1)_{t_1} = \left(\frac{dm_o}{dt}\right)_o \int_{t_1}^{t_2} \frac{C_1}{C_o} dt$$

where $(m_1)_{t_2} - (m_1)_{t_1}$ represents a difference in mass of the component of interest passing through the cross sectional area 22 from time $t_1$ to $t_2$.

Under the actual flow conditions wherein variations of flow in the main fluid flow tube occur, it is difficult to maintain the tracer mass injection rate $(dm_o/dt)_o$ equal to the mass flow rate of the tracer through the cross sectional area 22.

When restrictions are placed on the flow system such as a constant temperature and pressure or a constant flow rate, the volume being considered is that volume between the tracer injection site and the cross sectional area where analysis occurs either directly in the main flow stream, or at an analyzer or a collecting container at the end of a sampling line attached to the main flow tube.

If the distance between the point of injection of the tracer and the point at which the sample is removed is small in the presence of good mixing, or there is no extended period of flow stoppage or fast variations in flow rate, especially if they occur frequently, the difference between $(dm_o/dt)$ and $(dm_o/dt)$ usually will not be great. In this regard, it is desired to keep $(dm_o/dt)$ as constant as possible at some one known value.

Evaluation of the concentration ratio time, integral provided above over the period $t_1$ to $t_2$ is usually not possible with a predetermined mathematical equation since no prior information is available for $C_1/C_o$ as a function of t. Since the ratio $C_1/C_o$ varies with time, it is necessary to take the ratio of the analyzer output signal, usually voltage, of two analyzers, which must be of the continuous type for concentrations that vary, one for the tracer and one for each of the components of interest whose total mass flow in the time interval $t_1$ to $t_2$ is to be determined. The output of each analyzer is then multiplied by a proportionality factor, K, such that if voltages $V_1$ and $V_2$ are the voltages from the analyzers, the following equation is true:

$$C_1/C_o = k_1/k_o V_1/V_o$$

For the sake of simplicity, the proportionality factors should be made equal so they cancel out.

Since the element of volume for both the tracer and the component of interest is the same, the rates of concentrations can be written as the ratio of their masses, i.e., $$\frac{C_1}{C_o} = \frac{\frac{m_1}{v}}{\frac{m_o}{v}} = \frac{m_1}{m_o}$$

which is usually a disadvantage because concentrations are easier to obtain than mass, especially on a continuous basis. In the above equation, v is the total volume.

In addition to stating these concentration ratios as voltage or current ratios (assuming the proportionality factors $k_i$ and $k_o$ are equal), they can be written as any ratios which are proportional to the concentration or mass ratios, e.g., in the case of absorption of electromagnetic radiation, nuclear radiation, etc., where $I_1/I_o$, absorption per unit time intensity ratio, is to be used $$C_1/C_o = k_1 I_1 / k_o I_o \qquad 5$$

In addition to expressing the concentration in units of mass per unit volume, they can also be expressed as volume fraction, percent volume, parts per million by volume, etc., all multiplied by the density of the component of interest and usually a proportionality factor, e.g., $$\frac{mass_1}{volume_T} = \frac{density_1 \, volume_1}{volume_T} = \frac{D_1 V_1 10^6}{10^6 V_T} = \frac{D_1}{10^6} ppm_1$$

where $ppm_1$ refers to parts per million of component 1 expressed in units of volume, with T representing total.

The resulting proportionality signal, equal to the ratio of the above concentrations, is first multiplied by the mass injection rate of the tracer and then integrated over the time interval $t_1$ to $t_2$. If the mass injection rate of the tracer is constant, proportionality signal can first be integrated and then multiplied by the constant mass injection rate of the tracer, $(dm_o/dt)_o$ which is equal to $(dm_o/dt)$, which is known. The result of this final multiplication is the total mass emission value of the component of interest which has passed through the cross sectional area 22 between the time $t_1$ and $t_2$.

As a consequence of the constant mass flow rate of tracer in the main stream, which can also be expressed in terms of a definite number of moles, i.e., a definite number of molecules, there must also exist a constant total molecular flow of all the components present in the main fluid flow, expressed in terms of a constant number moles of components per unit of time. In this regard, constant flow is considered to mean not changing. The flow can be different in linear velocity along the path of travel thereof since if the cross sectional area is reduced, the linear fluid velocity is increased through this area. By knowing the volumetric flow rate, either the linear velocity or cross sectional area can be determined as long as the other is known.

With gases, low temperatures and high pressures produce the greatest deviation from constant total molecular flow rate due to their effect, on or variation of, the compressibility factor of the gases. Thus, operation of the system 10 at low temperatures and high pressures is to be avoided. In addition, to prevent condensation or absorption of the tracer, as well as those of the other species present, the former, mainly higher temperatures and lower pressures, are preferred.

In the case where the mass flow rate of the tracer, the total pressure and temperature are all held constant, the volumetric flow rate is also constant, assuming ideal fluid behavior, which assumption is usually valid for most fluids wherein only a slight molecular interaction is present. As a result of this constancy in the physical conditions of the tracer concentration, $C_o$, this term can be brought out in front of the integral sign, so that the above final equation for determination of total mass flow becomes the equation indicated below:

$$(m_1)_{t_2} - (m_1)_{t_1} = \left(\frac{dm_o}{dt}\right)_o \frac{1}{C_o} \int_{t_1}^{t_2} C_1 \, dt$$

This equation is true also if the mass injection rate of the tracer were not constant since $$\frac{dV}{dt} = \left(\frac{dm_o}{dt}\right)_o \frac{1}{C_o}$$

i.e., the volumetric flow rate in the main fluid flow tube 12 is constant.

$$(m_1)_{t_2} - (m_1)_{t_1} = \frac{dV}{dt} \int_{t_1}^{t_2} C_1 \, dt$$

If $C_1$ is also constant under the same conditions; that is, if the mass emission rate of 1, i.e., component $(dm_1/dt)$ from a source is constant, $C_1$ can also be brought in front of the integral sign and only an integration of the time differential is necessary, so that the final total mass flow equation becomes:

$$(m_1)_{t_2} - (m_1)_{t_1} = \left(\frac{dm_o}{dt}\right)_o \frac{C_1}{C_o}(t_2 - t_1)$$

If the mass emission rate of the component of interest is constant at the source of the smokestack, etc., its concentration can still vary, since the volumetric flow rate at the source can continuously undergo change. If sufficient inert fluid is added to the main flow tube to produce a constant volumetric flow rate, the concentration of component 1 becomes constant for the specified condition.

In the case where the volumetric flow rate of the main fluid flow at a constant temperature and pressure is constant $$\left(\frac{dm_o}{dt}\right)/C_o$$

is also constant. In such cases, the main volumetric flow can be calibrated first for total volume flow with the equation $$\left(\frac{dm_o}{dt}\right) \frac{1}{C_o}(t_2 - t_1).$$

The concentration of the component of interest can then be obtained and integrated over the time of $t_1$ to $t_2$. The product of this total volume and the average concentration of $C_1$ will then give the total mass. In combustion processes, the fuel mass or a constant fraction thereof could be used as the source of the mass of the injected tracer and the above volume or mass determination can be made. With such volume or mass determinations, only approximate values can be obtained if carbon particles are produced at a sufficient rate and not entered into the appropriate mathematical equation.

Instantaneous mass or volume flow rates can be determined by the tracer injection method with knowledge of the mass injection rate of the tracer component or its equivalent, its concentration (in units equivalent to mass per unit volume), and where in the flowing fluid the injection occured in order that its concentration can be determined in that unit of volume.

For instantaneous mass flow determinations, the following equation is used along with the aforementioned requirements:

$$\left(\frac{dm_1}{dt}\right) = \left(\frac{dm_o}{dt}\right)\frac{C_1}{C_o}$$

For instantaneous volume flow determination, in addition to the above, the temperature and pressure at the time when the concentration is determined and at the time the instantaneous volume flow is desired, are also needed if they undergo a change, along with the basic equation $$\left(\frac{dV}{dt}\right) = \left(\frac{dm_o}{dt}\right)\frac{1}{C_o}$$

When the tracer component used for injection undergoes a chemical or nuclear reaction it becomes necessary to determine if the extent of the reaction is significant at the time of analysis for obtaining the desired accuracy. If the extent of the chemical reaction is sufficient so it cannot be ignored for the accuracy desired, calculations are directed either to (1) express the concentration of both the unreacted original tracer material and one or more of its decomposition products, all in terms of the original injected tracer material, or (2) express both the concentration of the unreacted injected material and under some conditions that of one or more decomposition products, all in terms of the concentration of one of the designated atom-containing decomposition products. The first approach would be to determine the concentration of all components present at a significant concentration which contain the same atom as the designated atom in the injected tracer.

In some cases the tracer is already part of the original system, for example, in a combustion process where the fossil fuel or its decomposition products act as the injected tracer in addition to its use as a heat (including pressure at times) producing substance. Here the injection is into a reactor which may be a furnace, an engine, etc. Consideration of the fuel or its decomposition products as the tracer is all a matter of choice. In this case, the reactants would be mainly hydrogen-carbon compounds and oxygen with only carbon dioxide and water being formed (assuming complete combustion and only matter containing hydrogen, carbon and oxygen as the reacting starting materials).

Commercial fossil fuels may contain small amounts of other products besides carbon and hydrogen, e.g., sulfur, phosphorus, etc., as a result, other products containing these can be formed as part of the decomposition products. Since complete combustion usually does not occur for fossil fuel, other carbon containing compounds in addition to carbon dioxide exist at a significant concentration as a result of a combustion reaction. They must also be analyzed and considered in the appropriate calculations if a significant error would result in its absence. These products would most likely be carbon monoxide, elemental carbon, newly formed hydrocarbons, oxygenated hydrocarbons, etc., and products containing various amounts of other atoms in addition to those of carbon, hydrogen and oxygen (e.g., $NH_3$, $H_2S$, $SO_2$, NO, etc.), and also some unreacted fossil fuel. Since there is tremendous amount of fossil fuel used for the purpose of producing energy, specific calculations will be given to illustrate its use also as a tracer in flow measurement.

Even though a number of approaches to do this can be found in various books discussing combustion and combustion engines in addition to examples in the chemical literature, one will be discussed in detail for the purpose of clarity.

Consider the burning of a mixture of pure hydrocarbon in air having an average empirical formula of $C_5H_{12}$. The average composition of carbon and hydrogen in this or other pure mixtures or compounds can be determined in a number of ways by chemical analysis. The combustion process can be expressed with the following unbalanced chemical equation:

$$C_5H_{12} + O_2 + N_2 \rightarrow CO_2 + CO + CH_4 + C_5H_{12} + H_2O + N_2 + O_2 + CH_2O + NO + NH_3$$

Select one atom (e.g., carbon) in the starting material of interest (i.e., $C_5H_{12}$) and equate the mathematical product of the number of moles of this starting material times the number of carbon atoms (i.e., 5) found in the molecule (i.e., $C_5H_{12}$) to the sum of the individual mathematical products of the number of moles of each chemical product (containing one or more carbon atoms) times its number of carbon atoms per molecule. In cases where a significant amount of the chemically combined fossil fuel carbon is transformed into elemental solid carbon particles, special methods of analysis must be used or some correction factor for this ignored quantity of carbon must be applied. For example, we have

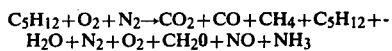

$$\left[\left(\frac{5\text{ moles}_C}{1\text{ mole}_{C_5H_{12}}}\right)\text{moles}_{(C_5H_{12})i}\right]_{reactants} =$$

$$\left[\left(\frac{1\text{ mole}_C}{1\text{ mole}_{CO_2}}\right)\text{moles}_{CO_2} + \left(\frac{1\text{ mole}_C}{1\text{ mole}_{CO}}\right)\text{moles}_{CO} + \right.$$

$$\left(\frac{1\text{ mole}_C}{1\text{ mole}_{CH_4}}\right)\text{moles}_{CH_4} + \left(\frac{1\text{ mole}_C}{1\text{ mole}_{CH_2O}}\right)\text{moles}_{CH_2O} +$$

$$\left.\left(\frac{5\text{ moles}_C}{1\text{ mole}_{C_5H_{12}}}\right)\text{moles}_{(C_5H_{12})f}\right]_{products}$$

where "i" and "f" refer to the initial and final states of the component before and after reaction, respectively. This terminology is used to designate that portion of an original component which has not undergone any change. Each term in the above molar equation can be divided by the component of volume in which each of the above components, i.e., $C_5H_{12}$, $O_2$, $N_2$, $CO_2$, CO, $CH_4$, $H_2O$, $N_2$, $O_2$, $CH_2O$ and NO, is present, resulting in units of moles per unit volume. Next, one can express the number of moles as mass per unit molecular weight for each component. This can be followed by expressing the ratio of mass per unit volume as a unit of concentration; the new set of units for each term will be concentration per unit molecular weight. In order to avoid confusion between the symbol "C" as used for carbon, the uncapitalized term "con" will be used wherever concentration needs to be used.

$$5\left(\frac{con}{M}\right)_{(C_5H_{12})i} = \left(\frac{con}{M}\right)_{CO_2} + \left(\frac{con}{M}\right)_{CO} +$$

-continued $$\left(\frac{con}{M}\right)_{CH_4} + \left(\frac{con}{M}\right)_{CH_2O} + 5\left(\frac{con}{M}\right)_{(C_5H_{12})f}$$

Therefore, $$con_{(C_5H_{12})i} = \frac{1}{5}\left(\frac{M_{(C_5H_{12})}}{M_{(CO_2)}}\right)con_{CO_2} +$$

$$\frac{1}{5}\left(\frac{M_{(C_5H_{12})}}{M_{(CO)}}\right)con_{CO} + \frac{1}{5}\left(\frac{M_{(C_5H_{12})}}{M_{(CH_4)}}\right)con_{CH_4} +$$

$$\frac{1}{5}\left(\frac{M_{(C_5H_{12})}}{M_{(CH_2O)}}\right)con_{CH_2O} + con_{(C_5H_{12})f}$$

where con is defined as concentration and M as Molecular weight of the specie designated in the subscript. After substituting the known molecular weights in the above mathematical equation $$con_{(C_2H_{12})i} = \frac{1}{5}\left(\frac{72}{44}\right)con_{CO_2} + \frac{1}{5}\left(\frac{72}{28}\right)con_{CO} +$$

$$\frac{1}{5}\left(\frac{72}{16}\right)con_{CH_4} + \frac{1}{5}\left(\frac{72}{30}\right)con_{CH_2O} + con_{(C_5H_{12})f}$$

When the concentration of the tracer, i.e., $con_{(C_5H_{12})i}$ in units of mass per unit volume, is inserted for $C_o$ in the basic total mass flow equation, i.e., $$(m_1)_{t_2} - (m_1)_{t_1} = \int_{t_1}^{t_2}\left(\frac{dm_o}{dt}\right)\frac{C_1}{C_o}\,dt$$

we obtain $$(m_1)_{t_2} - (m_1)_{t_1} = \int_{t_1}^{t_2}\left(\frac{dm_{C_5H_{12}}}{dt}\right)\frac{con_1}{con_{(C_5H_{12})i}}\,dt$$

where $con_{(C_5H_{12})}$ is to expressed in terms of its initial concentrations or its equivalent concentration (i.e., assuming it has not undergone any change since its time of injection) which can be calculated with both qualitative and quantative data on the resulting carbon containing decomposition products (including also the unreacted $C_5H_{12}$).

$$(m_1)_{t_2} - (m_1)_{t_1} = \int_{t_1}^{t_2}\left(\frac{dm_{C_5H_{12}}}{dt}\right)\frac{con_1}{\frac{1}{5}\left(\frac{72}{44}\right)con_{CO_2} + \frac{1}{5}\left(\frac{72}{28}\right)con_{CO} + \frac{1}{5}\left(\frac{72}{16}\right)con_{CH_4} + \frac{1}{5}\left(\frac{72}{30}\right)con_{CH_2O} + con_{(C_2H_{12})f}}\,dt$$

Another approach would be to equate the hydrogen containing molecules so the number of hydrogen atoms at the start is equal to those at the end of any reaction. Since water, which is one of these combustion products, acts very "non-ideal" and tends to undergo a condensation reaction, it is usually not the preferred component to analyze, thereby hydrogen is usually not the chosen designated atom.

If the mass injection rate of the tracer is constant, the above equation becomes:

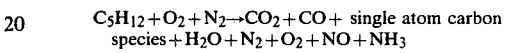

besides using carbon, hydrogen, or both as the products to be analyzed for calculating mass or volume flow, a mixture or pure component can be distributed throughout a composition such as a fossil fuel for the purpose of participating as a tracer. Rather than run an analysis for each of the organic species present in the combustion reaction, they could be analyzed for the total carbon concentration by means of a carbon ionization analyzer; this approach would be more direct in a number of cases and it would be satisfactory as far as tracer calculations are concerned. If our previous unbalanced chemical equation is written with this idea in mind, we obtain:

$C_5H_{12} + O_2 + N_2 \rightarrow CO_2 + CO +$ single atom carbon species $+ H_2O + N_2 + O_2 + NO + NH_3$ In regards to determining the mass flow of the component of interest, this could also be (1) one of the components of the fuel or its reaction products (e.g., CO or $C_5H_{12}$), (2) a reaction product of combustion but not of the fuel (e.g., NO), or a product originally present before the combustion reaction occurred (e.g., in the air used for combustion).

The same basic mass equation given previously is used for particulate material; that is, a continuous analyzer is calibrated with a standard smoke, suspension, optical filter of a predetermined transmission (intensity and wavelength) which is equivalent to a definite concentration of type (size, shape, etc.) of the particulate material. An effective $C_1$ can be determined photometrically and expressed mathematically as $C_1 = (1/a_{1l})\log_{10} 1/T$, where T, the transmittance, is defined as the ratio of the intensity of the transmitted light per unit of incident light, "l" is the path length of the light absorption medium, and $a_1$ is the average absorption coefficient of the particulate material whose mass is being determined. If $C_1$ and "l" are expressed in units of mass per unit volume and length respectively, then $a_1$ will have units of area per unit mass. It is important here that the heterogeneous composition is uniform over the cross sectional area. For high smoke concentration, a shorter path length with greater width would be preferred. Shorter path lengths would decrease the likelihood of two or more particles blocking the same path of the directed, transmitted radiation (either electromagnetic or radioactive).

The total volume flow of the main fluid flow may also be determined for most compositions by the same $$(m_1)_{t_2} - (m_1)_{t_1} = \left(\frac{dm_{C_5H_{12}}}{dt}\right)\int_{t_1}^{t_2}\frac{con_1}{\frac{1}{5}\left(\frac{72}{44}\right)con_{CO_2} + \frac{1}{5}\left(\frac{72}{28}\right)con_{CO} + \frac{1}{5}\left(\frac{72}{16}\right)con_{CH_4} + \frac{1}{5}\left(\frac{72}{30}\right)con_{CH_2O} + con_{(C_5H_{12})f}}\,dt$$

In the case where the only carbon material formed was carbon dioxide, the final equation becomes:

general tracer technique used in determining the total mass of a component of interest. In such a determination, the flow system illustrated in FIG. 1 down through the pump 26 is utilized. Following the pump 26, a single analyzer 72, reciprocal detector 73, reciprocal proportionality factor 77, multiplier 75, time integrator 74, mass rate signal producing circuit 76 and multiplier 78, as shown in FIG. 2, are necessary to produce a total value output signal 79. It should be stated that if the volume flow of the incoming main fluid is to be determined, no inert fluid can be added unless the volume flow is known and then subtracted from the total volume flow which results. The mathematical computations to illustrate the theoretical accuracy of such a system are simplified relative to the total mass computations.

In the case where it is desired to determine the total volume flow of the main fluid flow with a variable mass injection rate of the tracer, the system illustrated in FIG. 4 is utilized. In such a determination, the flow system illustrated in FIG. 1 down through the pump 26 is used. Following pump 26, a single analyzer 100, reciprocal detector 101, reciprocal proportionality factor 103, mass rate signal 104, multiplier 102, and time integrator 105 are necessary to produce a total output signal 106.

In developing a simplified mathematical equation for total volume flow of a component of interest, the same symbol definitions are used as in the mass determination. The following equations are true based on reasoning similar to that for mass flow determination:

$$m_o = C_o V$$

$$\left(\frac{dm_o}{dt}\right) = C_o \left(\frac{dV}{dt}\right)$$

$$\left(\frac{dV}{dt}\right) = \left(\frac{dm_o}{dt}\right)\frac{1}{C_o}$$

In order to give meaning to any numerical value for volume flow, total or instantaneous, especially for easily compressible fluids, both temperature and pressure must be stated. If either or both the temperature and pressure are continuously varying at the point where the quantity of volume is assigned in the flow system, an exceedingly detailed continuous data bank would be needed. To avoid this the description will deal with constant temperature and pressure at the point of assigning the numerical values, and if variations of temperature or pressure do occur, the volume should be thought of as being continuously referred back to some one set of conditions.

The total volumetric flow from time $t_1$ to $t_2$, that is, the time integral of the last above equation is given below:

$$\int_{(V)_{t_1}}^{(V)_{t_2}} dV = \int_{t_1}^{t_2} \left(\frac{dm_o}{dt}\right) \frac{dt}{C_o}$$

When the mass flow rate of the tracer passing through the cross sectional area 22 equals a constant mass injection rate of the tracer, that is, $(dm_o/dt) = (dm_o/dt)_o$ equals a constant independent of time, the following final volumetric equation results:

$$(V)_{t_2} - (V)_{t_1} = \left(\frac{dm_o}{dt}\right)_o \int_{t_1}^{t_2} \frac{1}{C_o} dt$$

Under the condition where $(dm_o/dt)_o$ is equal to $(dm_o/dt)$ i.e., the mass rate of tracer injection is equal to the rate it passes through the cross sectional area 22, the following equation results:

$$(V)_{t_2} - (V)_{t_1} = \int_{t_1}^{t_2} \left(\frac{dm_o}{dt}\right)_o \frac{1}{C_o} dt$$

where the mass injection rate of the tracer can be a variable, but it must be known in addition to its concentration, $C_o$, both as a function of time.

If the temperature, pressure and volumetric flow rate, (assuming ideal fluid behavior does result with the addition of $C_o$) are constant, then $$\left(\frac{dm_o}{dt}\right)/C_o$$

is also constant and it can be brought in front of the integral sign followed by its time integration as indicated in the following equation:

$$(V)_{t_2} - (V)_{t_1} = \left(\frac{dm_o}{dt}\right)_o \frac{1}{C_o} \int_{t_1}^{t_2} dt = \left(\frac{dm_o}{dt}\right)_o \frac{(t_2 - t_1)}{C_o}$$

The above integral is evaluated in the same manner as described for the total mass calculation with the exception that the concentration of only one component, that is, the tracer, is continuously analyzed. If the mass flow rate of the tracer passing through this cross sectional area only equals its mass injection rate, but is not constant, the first equation would have to be used unless the tracer mass injection rate is an average value; therefore, it is placed outside the integral sign. What is being said is that if the tracer injection rate varies, the $(dm_o/dt)$ term must be integrated along with $C_o$. If the pressure, temperature and flow rate of the tracer is constant, the ratio of the mass injection rate and the concentration resulting from that particular portion as analyzed for at the cross sectional area 22 is also constant.

If the total volumetric flow between times $t_2$ and $t_1$ are determined with the above equation, the total volumetric flow at a constant temperature and pressure can be computed for a known longer period of time with the following equation wherein $V_{t3}$ and $V_{t2}$ and $V_{t1}$ are the total final, intermediate and initial volumes and where $t_3$, $t_2$ and $t_1$ are the final, intermediate and initial times, respectively:

$$V_{t3} - V_{t1} = (V_{t2} - V_{t1}) \frac{(t_3 - t_1)}{(t_2 - t_1)}$$

This method of determining volumetric flow is useful in checking the constancy of the volumetric flow rate of the fluid for a definite temperature and pressure by continuously analyzing for $C_o$ and checking the constancy thereof.

In addition to being able to determine the instantaneous volumetric flow rate, it is also possible to determine the instantaneous linear velocity of the flowing fluid at the cross sectional area through which it passes. To determine either the linear velocity or the cross sectional area, one of the two should be known in addition to having the information needed to calculate the instantaneous flow rate. The following equations are used to make these two calculations:

$$\left(\frac{dl}{dt}\right) = \frac{1}{A} \left(\frac{dm_o}{dt}\right) \frac{1}{C_o}$$

$$A = \frac{1}{\left(\frac{dl}{dt}\right)} \left(\frac{dm_o}{dt}\right) \frac{1}{C_o}$$

where $(dl/dt)$ is the instantaneous linear velocity of the flowing fluid across the cross sectional area, A is the cross sectional area of interest, $(dm_o/dt)$ is the instantaneous mass flow rate of the tracer across the cross sectional area, and $C_o$ is the tracer concentration in units of mass per unit volume. One application would be to determine the total or instantaneous volume or mass flow of blood in the blood vessels of animals, including its instantaneous or average linear velocity, and the cross sectional area of the blood vessel at the point or points of interest. The main flow tube would be considered to be the blood vessel.

The tracer can be injected with blood, saline solution, and the like. It can be (1) the blood itself which is different from that already present, saline solution at a higher concentration than that which is already present or of a different chemical composition, or (2) any of these with a radioactive tagged atom, or (3) a body foreign to the blood, or (4) a substance already in the body like one of the minerals, halides, etc., vitamins, enzymes, and the like. This method would be carried out by injecting at a known mass rate, preferably constant, usually through a tube, e.g., hypodermic needle, and some of the flow is removed further downstream through another tube usually of the same type. Either continuous monitoring can be applied or a container sample can be collected followed by a single analysis.

Although the ratio of the concentrations, that is, $C_1/C_o$, in the above equations refers to the concentrations of the fluid which is present in the main flow stream, the ratio should not be different at different temperatures and pressures in the analyzers as long as all analyzers have the fluid from the unknown mixture at the same temperature and pressure at which they were calibrated. This assumption is made assuming ideal fluid behavior, which is a good approximation in most cases if the variation in properties is not too great.

The concentration of tracer and component of interest, discussed in all the equations referred to so far, are for those conditions within the main flow tube. In order to express concentrations in terms of the conditions in the analyzer, assuming they are not the same conditions of temperature and pressure as in the main flow tube, the following equation which can be derived easily, can be used if gases are involved:

$$C_o = \frac{M_o 10^{-6}}{R Z} \cdot \frac{(P)(ppm)_o}{(T)}$$

where $C_o$, $M_o$, P, T, $(ppm)_o$ and Z are the tracer concentration (expressed in mass per unit volume), tracer molecular weight, ideal gas constant, total pressure, absolute temperature, tracer concentration in ppm by volume (same in main flow stream as in analyzer) and compressibility factor, respectively. As can be seen here, the pressure and temperature in the main flow tube (especially when gases are involved) enter into this equation. It is necessary to use this correction equation if either or both temperature and pressure are different in the main flow tube than in the analyzer compartment, when a single concentration variable is present in the equation, e.g., in the total volume flow equation, but if a ratio of concentrations are used, as in the mass flow equation, it would usually not matter.

Another means of expressing the tracer concentration (mass per unit volume) of a gaseous system in the main flow tube and analyzer is:

$$\frac{(C_o) 2}{(C_o) 1} = \frac{Z_1 P_2 T_1}{Z_2 P_1 T_2}$$

where the subscripts of 2 and 1 refer to the analyzer and main flow stream, respectively. Removal of the compressibility factors in this equation is usually possible by using conditions of temperature and pressure and fluids which are about the same in both the analyzer and the main flow tube. If the component used as the tracer is already present in the main fluid flow, then the following equation is used for the total mass flow, provided that the tracer mass injection rate is constant.

$$(m_1)_{t_2} - (m_1)_{t_1} = \left(\frac{dm_o}{dt}\right)_o \int_{t_1}^{t_2} \frac{C_1}{(C_a - C_b)_o} dt$$

and the following equation is used for the total volume flow:

$$(V)_{t_2} - (V)_{t_1} = \left(\frac{dm_o}{dt}\right)_o \int_{t_1}^{t_2} \frac{1}{(C_a - C_b)_o} dt$$

If $(C_a - C_b)_o$ is a constant in either of the above volume or mass flow equations, it can be brought in front of the integral sign. In the case where the component $C_1$ and the added tracer are of the same kind; that is, $c_1 = C_b$, $C_a - C_b = C_a - C_1$.

Here $C_a$ is the sum of the concentrations of: the tracer component added and that which was already present in the main flow, and $C_b$ is the concentration of the tracer component which was already present. All the values of $C_a$, $C_b$ and $C_1$ must be expressed under the same conditions of temperature and pressure and in the same units of concentration. The remaining symbols have the same meaning as before.

In order to measure the increase in concentration of the tracer due to its injection at a constant mass rate, it is continuously sampled at a point before the tracer injection site and at a point where the tracer has become a part of the flowing uniform composition. For example, using a continuous flow analyzer with dual flow cells, it is possible to cancel out the effective upstream concentration of the tracer component which is present upstream of the site where the tracer is to be injected at a constant mass rate. Here the reference flow cell has the original fluid passing through it from before the injection and the sample flow cell has a mixture of the original plus that with the tracer addition, passing through it. If the tracer and component of interest are to be the same substance, a quantity of injected tracer should be sufficiently great so the increase of tracer concentration can be calculated with sufficient accuracy.

When a variable mass injection rate is used for the tracer when it is already present, the same mass and volume flow equations can be used with the exception that $(dm_o/dt)$ is behind the integral sign rather than before. Unless the tracer mass injection rate produces a concentration that is sufficiently greater than that which is already present, it will be difficult to relate the variable concentration increase of the tracer in the analyzer to its variable mass injection rate which produced it at a definite time interval prior to its analysis. If all of this is based on a constant fluid flow in the main flow tube at a constant temperature and pressure, then $$\frac{\left(\frac{dm_o}{dt}\right)}{(C_a - C_b)_o}$$

can be brought outside the integral sign.

The time required for a fluid which has a constant (assuming no temperature and pressure variation) volumetric flow rate in the main flow tube to reach and pass through the analyzer flow cells from the sample and reference taking point should be the same for this dual cell analyzer and others used in the same computation, i.e., theoreictally the same original composition (except for the tracer because of its downstream addition) should reach both analyzer flow cells at the same time, including any other analyzer determining the concentration of other components of interest. When there is an injection of the tracer, there should be an increase in concentration in that sampling line which is located after the main flow has undergone a mixing process. For combustion processes where determination of $CO_2$ concentration is not necessary, the use of $CO_2$ as the tracer is practical, assuming the temperature of the flow system is at a high enough temperature to prevent condensation and absorption resulting in a significant percentage error.

In addition to continuous sampling, analysis and integration of instantaneous concentration values of the components of interest from the main flow stream, it is also possible to collect in chemically inert containers (usually flexible for a gas and rigid for a liquid) the total of the instantaneous sampling fluid.

The mixture continuously coming into the container is either (1) mixed continuously and the instantaneous composition of the mixture is continuously analyzed non-destructively, i.e., analysis has no effect on it, and the analyzed composition is returned to the original container, or (2) the total mixture is mixed uniformly, then it is analyzed. In the first method where the instantaneous fluid is collected during the period from $t_1$ to $t_2$ in the container, the same equation $$(m_1)_{t_2} - (m_1)_{t_1} = \left(\frac{dm_o}{dt}\right)_o \int_{t_1}^{t_2} \frac{C_1}{C_o} dt$$

is used but the instantaneous concentrations $C_1$ and $C_o$ are not the same, since they are instantaneous average concentration values resulting from the mixing of additional fluid from the sampling line with the total of that present previously in the container. For the second method we substitute the equation $$\int_{t_1}^{t_2} \frac{C_1}{C_o} dt = \frac{\overline{C_1}}{\overline{C_o}} (t_2 - t_1)$$

into the above. Therefore, $$(m_1)_{t_2} - (m_1)_{t_1} = \left(\frac{dm_o}{dt}\right)_o \frac{\overline{C_1}}{\overline{C_o}} (t_2 - t_1)$$

where $\overline{C_1}/\overline{C_o}$ refers to the ratio of the average value of $C_1$ divided by the average value of $C_o$.

In the second case, the same result is obtained as was obtained in the first, but only one set of analysis has to be run, i.e., the concentration of the component of interest $C_1$, and concentration of the tracer $C_o$; these are average values of the components in the main flow system. After the fluid is collected, it is mixed, e.g., if it is a liquid it can be stirred or shaken and if a gas it can be mixed by pressing on the flexible bag a number of times to mix the gas. Since only one concentration value is needed for each component to be analyzed, either a continuous or individual single sample analyzer need be used.

In these methods of collecting the fluid, the same principles hold as in the direct integration method including the equations (except the concentrations here are average, or instantaneous average values rather than instantaneous ones of a totally new portion of a fluid), the ratios $C_1/C_o$ are also not affected by changes of temperature and pressure between the main flow stream and the analyzers, but in the collection of the sample, the temperature, pressure and flow rate should be held at a constant value after the time the sample is removed from the main flow tube to the time it is analyzed for easier operation and usually better results. By storing the collected sample in a container and allowing it to stand for a period of time, it can be permitted to react if this is desirable (e.g. dissolving $NO_x$ auto exhaust gases in a Saltzmar reagent); but in most cases, reaction due to storage is a disadvantage; therefore, analysis is performed as soon as possible after collection of the sample.

It should be noted here that the equations $$\int_{t_1}^{t_2} \frac{C_1}{C_o} dt = \frac{\overline{C_1}}{\overline{C_o}} \int_{t_1}^{t_2} dt = \frac{\overline{C_1}}{\overline{C_o}} (t_2 - t_1)$$

are true if $C_o$ is a constant since the average of the sum of a number of ratios, usually does not equal the average of the sum of the values in the numerator divided by the average of the sum of the values in the denominator. The case where all denominator values are equal and constant is an exception. This is true when both the tracer mass injection rate and the main fluid flow rate are constant.

If a constant fraction of the fluid from the main flow stream at a constant temperature and pressure is to be collected in a container, it is possible to inject the tracer at a non-constant mass rate, and the general mass equation, i.e., $$(m_1)_{t_2} - (m_1)_{t_1} = \int_{t_1}^{t_2} \left(\frac{dm_o}{dt}\right) \frac{C_1}{C_o} dt$$

under conditions of a constant main fluid flow rate, resulting in $$\frac{\left(\frac{dm_o}{dt}\right)}{C_o}$$

equaling a constant, becomes $$(m_1)_{t_2} - (m_1)_{t_1} = \frac{\left(\frac{dm_o}{dt}\right)}{C_o} \int_{t_1}^{t_2} C_1 \, dt$$

As with the non-collected container samples, if the volumetric flow rate is constant in the main flow tube, the tracer should pass the cross sectional area at a rate equal or approximately equal to the mass injection rate of the tracer, but at a different time. The time delay between injection of the tracer and removal of the sample at the cross sectional area is based; (1) on the distance between tracer injection site and location of the cross sectional area where the tracer is removed, and (2) on the main fluid flow rate.

The use of a light beam having both a reference and one or more sample wavelength bands where the reference wavelength band is not absorbed by a moving fluid but is blocked by particles within the fluid, while the tracer wavelength band and any number of component of interest wavelength bands are absorbed individually by the tracer and by the components of interest respectively in the moving fluid and are also blocked by the particles within the moving fluid, has also been considered.

By taking a log ratio of the intensities of the transmitted wavelength bands or a direct ratio of the absorbed wavelength bands of the sample and reference component, the effect of the particles present in the flowing main fluid can be cancelled out, and by using the sample beam wavelength for the tracer component with or without another sample beam wavelength for the component of interest, the total or instantaneous volume or mass flow, respectively, can be determined and a signal can be generated which is proportional to the concentration of the component of interest in a particle containing fluid, as for example, in the smoke stack of a power plant. For a combustion process the fuel or one or more of its oxidation products, e.g., $CO_2$, $H_2O$, $CO$, and unburned fuel can be used as the tracer. The reference wavelength should not be absorbed by any component (except the particles) whose concentration does vary over the time interval when the measurements are taken. The apparatus (not including the apparatus set forth in this specification) for this measurement can be supplied by the Environmental Data Corp. of California. It has a system which passes specific wavelength bands through the flowing fluid, e.g., that in a smokestack. The use of this method for volume or mass determination wherein a tracer is used is believed to be novel.

Direct Analyzer Calibration

This is a process where the total or instantaneous mass of one or more of the components present in a flowing fluid, and the total or instantaneous volume of a flowing main fluid can be measured.

This is done by using a calibrated flow system consisting of a main flow tube with the following attachments: a tracer component (or component of interest) injection site for injection at a constant mass rate during time of calibration, a sampling tube and pump to transfer a continuous flow to the analyzers if analysis is not made directly on main flow by sending an analyzing signal through it or monitoring one from it, a continuous flow analyzer for each component to measure instantaneous concentrations on a continuous basis or one or more multicomponent analyzers, a pumping system to maintain a continuous flow in the main fluid flow tube and extra fluid flow inlet to maintain a constant fluid flow, a mixer in main flow stream to mix main and inlet fluid with injected tracer fluid during analyzer calibration step. A constant temperature control system to maintain the flowing fluid at a constant temperature, a filter for particulate matter, and a vapor condenser at the entrance to the main flow tube may sometimes be necessary, depending on the composition of the main fluid. If this fluid is a gas, a critical orifice meter can be very useful to obtain a constant mass flow of an injected component, or a well-controlled gas regulator can be used. If the fluid is a liquid, a constant rate injection pump should be satisfactory.

Analyzers can be calibrated by the injection of the tracer at a constant mass rate and also for the component of interest, into the main flow tube, where it is mixed to a uniform composition, consisting of the extra injected tracer and main flow, followed by the transfer, usually with a pump, of a portion of this composition into the continuous flow analyzers connected in parallel (or direct flow stream) analysis by sending or receiving a signal through or from, respectively, the moving flow. The constant mass injection rate values become the analyzer meter readings for that component, in that analyzer-flow tube system.

Analyzers can also be calibrated on a mass per unit time basis by first calibrating them in the usual manner (i.e., by passing the calibration fluid directly into the analyzer and not first through the main flow tube stream) in terms of ppm by volume, or some other concentration units based on the mole. This method is useful if there are a number of gases or fluids for which the meters are to be calibrated, in units of volume per unit volume, here only one meter has to be calibrated by injecting a fluid at a known mass rate. To obtain this mass per unit time calibration on the other meters the following equation is used:

$$\left(\frac{dm_1}{dt}\right) = \left(\frac{dm_o}{dt}\right) \frac{M_1}{M_o} \frac{C_1}{C_0}$$

Symbol Definition $(dm_1/dt)$ and $(dm_o/dt)$ = instantaneous values of mass per unit time of component 1 and tracer (or reference component), respectively.

$M_1$ and $M_o$ = molecular weight of component 1 and tracer (or reference component), respectively.

$[C_1]$ and $[C_o]$ = concentration of component 1 and tracer (or reference component), respectively, expressed in terms of ppm by volume or some other mole dependent concentration.

If concentrations were expressed in units of mass per unit volume, the molecular weights would not be needed as part of the above mathematical equation and it becomes $$\left(\frac{dm_1}{dt}\right) = \left(\frac{dm_o}{dt}\right)\frac{C_1}{C_o}$$

which are the same equations as those which are used for the instantaneous mass flow determination.

For the determination of the total mass flow, either by the direct calibration of the analyzer-flow-tube system (i.e., the analyzer connected to the main flow stream) or indirectly by calibrating one analyzer with another, both connected in parallel to the main flow tube system, the following equation is used:

$$(m_1)_{t_2} - (m_1)_{t_1} = \int_{t_1}^{t_2} \left(\frac{dm_1}{dt}\right) dt$$

where ($dm_1/dt$) is the instantaneous mass flow rate reading on the meter of the analyzer for the component of interest (component 1).

For example, if a carbon monoxide analyzer has already been calibrated in the usual manner, then a definite mass per unit time of carbon monoxide is injected into the main flow tube continuously; the usual meter concentration (parts by volume) which corresponds to this constant mass injection value (i.e., mass per unit time), along with its molecular weight, can be used to determine the mass per unit time value of all the other analyzers because of the above equation.

As before, container samples can also be collected, analyzed, and the data can be used to determine total volume flow and total mass flow for a number of components present in a flowing fluid.

The procedure for this container method would be to inject the component of interest at a constant mass rate into a flow tube where the fluid is moving at a constant volumetric flow rate with temperature and pressure held constant (but may be different) at every point in the main flow tube and sampling line between the injection site and the point of analysis, pass a sample of this fluid continuously into a container, mix uniformly, analyze for the component or components of interest, designate on this analyzer at the meter reading the value of the mass injection rate of that component which was used. (Note: Before the component of interest is passed into the analyzer, the analyzer must be zeroed in with a similar fluid but not containing the component of interest, also the analyzer must be adjusted so the calibrating component of interest gives a reasonable response on its meter reading.)

Now that the flow analyzer container system is calibrated, a sample of the flowing fluid containing the component of interest is passed through this calibrated tube-analyzer system and is collected in a container, mixed to a uniform composition and analyzed with the same analyzer whose meter had been calibrated previously. This meter reading, due to the unknown sample, is multiplied by the length of time the sample was collected and this will give the number of grams of the component of interest that has passed through the flow tube during the time when collection of the sample occurred.

Another approach where a container sample is involved would be where a known total mass of tracer is injected at an unknown mass rate into a main fluid flowing at a constant flow rate (at a constant temperature and pressure) and mixed. A constant fraction of the total flow is passed continuously into a container, mixed, then analyzed for each component. With the following equation $$m_1 = m_o (C_1/C_o)$$

the total mass of component 1, $m_1$, passing through the cross sectional area is obtained by knowing how many grams of tracer were injected when the concentration of tracer in the container is $C_o$ and the concentration of component 1 is $C_1$, both in units of mass per unit volume, over the period of time a constant fraction of the flowing fluid is being collected.

DETERMINATION OF ENERGY TRANSFER

The amount of energy which a nonradiating substance gains or loses as it comes into contact with another substance is based on the temperature difference between the two substances, their masses, and their heat capacities and can be determined by the application of the formula $$\Delta E = \int_{T_1}^{T_2} m\, C_p\, dT$$

where $\Delta E$ is the amount of energy which is transferred by a flowing fluid, with a mass m, a heat capacity $C_p$, and an initial temperature $T_1$, to another substance with an initial temperature of $T_2$ during the time when the temperature of the flowing fluid changes from $T_1$ to $T_3$. The source for our purposes can be thought of, e.g., as a gas (with or without particulate matter) emitted from a smoke stack to the atmosphere, hot water or steam going to a lake or river, etc. It is seldom necessary to calculate the absolute energy of a system, but frequently it is necessary to know the total amount of energy transferred to another system or the total amount transferred in excess above that which an equal amount already present would have at the original initial temperature into which the energy transferring fluid is to pass.

The quantity of material and its heat capacity will determine what temperature change will occur within it when an external source of energy is added. For calculation of the amount or degree of thermal pollution, information regarding how much energy is transferred becomes important.

Starting with the basic total volume flow equation, i.e., $$(V)_{t_2} - (V)_{t_1} = \int_{t_1}^{t_2} \left(\frac{dm_o}{dt}\right)\frac{1}{C_o} dt$$

By multiplying this equation by D the density (mass) of the instantaneous total fluid of all components, the equation becomes $$(m)_{t_2} - (m)_{t_1} = \int_{t_1}^{t_2} D\left(\frac{dm_o}{dt}\right)\frac{1}{C_o} dt$$

By multiplying the non-time integrated form of this equation by the instantaneous heat capacity (energy per unit mass per unit degree) of the flowing fluid followed by a integration from temperature $T_1$ to $T_2$ then integrating from $t_1$ to $t_2$, we obtain the total energy transfer $\Delta E$ during the time from $t_1$ to $t_2$ due to only a temperature change from $T_1$ to $T_3$ $$\Delta E = (E_{T2})_{t_2} - (E_{T1})_{t_1} = \int_{t_1}^{t_2} \int_{T_1}^{T_2} C_p D \left(\frac{dm_o}{dt}\right) \frac{1}{C_o} dT dt$$

SYMBOLS $\Delta E$ = amount of energy transferred by flowing fluid to or from another substance.

$(dm_o/dt)$ = mass flow rate of tracer.

$C_o$ = concentration (mass per unit volume) of tracer at temperature $T_1$.

$D$ = density (mass per unit volume) of total instantaneous flowing fluid at temperature $T_1$.

$C_p$ = heat capacity (energy per unit mass per unit degree) at temperature $T_1$ and pressure $P$.

$t_1$ = initial time or start of measurement.

$t_2$ = final time or end of measurement.

$T_1$ = temperature of flowing fluid.

$T_3$ = final temperature of flowing fluid after having come in contact with a substance originally at a temperature $T_2$.

$T_2$ = temperature of fluid or other substance before coming into contact with flowing fluid (at $T_1$).

$dT$ = temperature differential of flowing fluid.

$dt$ = time differential of fluid when it is flowing.

To calculate the amount of energy being transferred from the source to the external environment at its prevailing temperature, some other reference temperature (i.e., $T_2$) can be chosen above or below that which the quantity of energy transfer is to be considered. The choosing of a variable environmental temperature (e.g., that of the atmosphere above a power plant smoke stack or that of moving or standing water in a lake or river) would offer more difficulty than establishing a constant reference temperature. This method can be used to calculate energy (heat, etc.) transfer to a solid material, e.g., a wall or the walls of a pipe through which or to which the fluid containing the tracer is flowing.

Computations become somewhat more difficult if what has been defined as temperature $T_1$ and $T_2$ vary with time.

For the simple case where $(dm_o/dt)_o$, and $T_2$ and $T_1$ are constant and the $D$ and $C_p$ are constant within the temperature range $T_1$ to $T_2$, the basic equation $$\Delta E = \left(\frac{dm_o}{dt}\right) C_p D \int_{t_1}^{t_2} \int_{T_1}^{T_2} \frac{1}{C_o} dT dt$$

If the flowing fluid rate is constant, it would be preferred to use the tracer injection method for one determination of flow rate, but if it is continuously varying, a constant mass tracer injection method is desirable, especially if, in fact, a tracer material is being added during the routine method of operation, such as burning fossil fuel in a power plant giving $CO_2$, etc., which is analyzed.

The procedure for this would consist of introducing a tracer into the flowing fluid, analyzing for this tracer concentration in the flowing fluid or by removing a sample continuously for this purpose, monitoring its temperature continuously and that of initial temperature of the material it is to come in contact with, (if the temperature of said material does not change, only one continuous temperature determination is necessary), and means for integrating the mathematical product of its heat capacity and density of the flowing fluid, tracer mass injection rate and reciprocal concentration of tracer, over the temperature range from $T_1$ to $T_2$ and the time interval involved.

TRANSFER OF RADIOACTIVE MATERIAL IN A FLOWING FLUID

For measuring the quantity of radioactivity being transferred, the same basic mass or volume equations can be used with some substitution, others can be developed in the same manner as with the basic mass or volume equation.

As in the derivation of the basic mass equation $$(m_1)_{t_2} - (m_1)_{t_1} = \int_{t_1}^{t_2} \left(\frac{dm_o}{dt}\right) \frac{C_1}{C_o} dt$$

the following equation can be derived by using $V = R_1/I_1$ in place of $V = m_1/C_1$ to obtain $$(R_1)_{t_2} - (R_1)_{t_1} = \int_{t_1}^{t_2} \left(\frac{dm_o}{dt}\right) \frac{I_1}{C_o} dt$$

where $(R_1)_{t_2}$ = radioactivity, i.e., the number of disintegration or photons emitted per unit time of component 1 transferred across the hypothetical cross sectional area in the main flow tube whereas $I_1$ = the intensity of the radioactivity of component 1 per unit volume.

If the component 1 interest is not radioactive but the tracer is, the following equation is used:

$$(m_1)_{t_2} - (m_1)_{t_1} = \int_{t_1}^{t_2} \left(\frac{dR_o}{dt}\right) \frac{C_1}{I_o} dt$$

where $(dR_o/dt)$ = rate of flow of radioactivity of the radioactive tracer (i.e., number of disintegrations or photons emitted per unit time), across the cross sectional area 22.

If both tracer and component of interest are radioactive, we have $$R_{1t_2} - R_{1t_1} = \int_{t_1}^{t_2} \left(\frac{dR_o}{dt}\right) \frac{I_1}{I_o} dt$$

As in the derivation of the basic volume equation $$V_{t_2} - V_{t_1} = \int_{t_1}^{t_2} \left(\frac{dm_o}{dt}\right) \frac{1}{C_o} dt$$

the volume $V = R_o/R_o$ can be substituted for $V = m_o/C_o$ and we obtain $$(V)_{t_2} - (V)_{t_1} = \int_{t_1}^{t_2} \left(\frac{dR_o}{dt}\right) \frac{1}{I_o} dt$$

As before if the mass injection rate of the tracer is constant over the time interval the measurement is being made, it can be brought outside the integral sign and calculations and the operational procedure becomes simpler. In addition the same approach can be used for container samples, previous presence of tracer, etc. As in the mass and volume cases the difference will lie in the use of radioactivity detectors versus the use of non-radioactive detector analyzers.

Where both the tracer and component of interest are radioactive, but different, one can think of them (1) as being of two different types of radioactivity, e.g., gamma and beta, or (2) where the same type of radioactivity is the same but the energies are different.

If there are many types of radiation occurring all at the same time, the total amount of radioactivity emitted can be determined (i.e., where $I_1$ in the previous equation refers to the total intensity, or it can be used for one or more of the various types of radiation which is simultaneously emitted), all based on the types of detectors being used.

Any number of commercial radiation analyzers can be used, Geiger counters, scintillation counters, etc., depending which is the most practical for the components and flow which is being monitored. As before, analysis may be done directly in the main flow tube, i.e., without removing a sample, or by removing a portion of the flow. Calibration is usually done by injecting at a known mass rate and calibrating the radiation analyzers by the response obtained. Either chemical or radioactive analysis can be carried out directly in the main flow tube or on a sample which is continuously removed from the main flow tube.

What I claim as my invention is:

1. The method of determination of the total mass flow of at least one component of interest in a reacted flowing main fluid in a period of time comprising the introduction of an analyzable tracer component comprising at least one component selected from the group consisting of a fuel and its reaction products at a known mass rate into a flowing main fluid, mixing the tracer component with the flowing main fluid, reacting the mixture of tracer component and the flowing main fluid in a reactor, analyzing the reacted mixture to determine the concentration of at least the tracer component and one component of interest in the reacted mixture, and time integrating the product of the ratio between the component of interest concentration and the tracer concentration, and the mass flow rate of the tracer over the time period in accordance with the formula $$(m_1)_t = (m_1)_{t_1} = \int_{t_1}^{t_2} \frac{C_1}{C_0} \frac{dm_0}{dt} dt$$

where $(m_1)_{t_2} - (m_1)_{t_1}$ is the total mass flow of the component of interest over the time period $t_1$ to $t_2$, $dm_o/dt$ is the mass flow rate of the tracer obtained from knowledge of the mass introduction rate of the tracer, and $C_1/C_o$ is the ratio of the concentration of the component of interest to the concentration of the tracer.

2. The method of claim 1 and further including passing the reacted mixture across a cross sectional area, analyzing the reacted mixture at the cross sectional area, and time integrating the product of the ratio between the component of interest concentration and the tracer concentration and the mass flow rate of the tracer over the cross sectional area over the time period in accordance with the formula set forth in claim 1.

3. The method set forth in claim 1, wherein the fluid flow rate of the reacted flowing main fluid is slowly changing.

4. The method set forth in claim 1, wherein the component of interest is at least one reaction product of said fuel.

5. The method set forth in claim 1, wherein the component of interest is at least one reaction product of the flowing main fluid.

6. The method set forth in claim 1, wherein the component of interest is the fuel.

7. The method set forth in claim 6, wherein the fuel is a fossil fuel.

* * * * *